(12) United States Patent
Yang et al.

(10) Patent No.: US 12,214,091 B2
(45) Date of Patent: Feb. 4, 2025

(54) SUPER ABSORBENT RESIN AND PREPARATION METHOD THEREOF

(71) Applicant: SHANDONG HAOYUE NEW MATERIALS CO., LTD, Shandong (CN)

(72) Inventors: Zhiliang Yang, Shandong (CN); Hao Yang, Shandong (CN); Yanyu Ma, Shandong (CN); Yang Yang, Shandong (CN); Xiang Zhang, Shandong (CN); Meiqin Yao, Shandong (CN); Jinshui Yao, Shandong (CN)

(73) Assignee: SHANDONG HAOYUE NEW MATERIALS CO., LTD, Jinan (CN)

( * ) Notice: Subject to any disclaimer, the term of this patent is extended or adjusted under 35 U.S.C. 154(b) by 1080 days.

(21) Appl. No.: 17/254,560

(22) PCT Filed: Jun. 22, 2018

(86) PCT No.: PCT/CN2018/092326
§ 371 (c)(1),
(2) Date: Dec. 21, 2020

(87) PCT Pub. No.: WO2019/241986
PCT Pub. Date: Dec. 26, 2019

(65) Prior Publication Data
US 2021/0268139 A1    Sep. 2, 2021

(51) Int. Cl.
| A61L 15/24 | (2006.01) |
| A61L 15/60 | (2006.01) |
| B01J 20/00 | (2006.01) |
| B01J 20/26 | (2006.01) |
| C08L 33/02 | (2006.01) |

(52) U.S. Cl.
CPC .............. *A61L 15/24* (2013.01); *A61L 15/60* (2013.01); *B01J 20/267* (2013.01); *A61L 2400/04* (2013.01); *B01J 2220/4812* (2013.01); *B01J 2220/68* (2013.01); *C08L 33/02* (2013.01)

(58) Field of Classification Search
CPC ...... A61L 15/24; A61L 15/60; A61L 2400/04; B01J 20/267; B01J 2220/4812; B01J 2220/68; C08L 33/02
See application file for complete search history.

(56) References Cited

U.S. PATENT DOCUMENTS

| 3,001,565 A * | 9/1961 | Beach .................. A61G 7/0503 383/7 |
| 4,911,699 A * | 3/1990 | Fenton .................... A61F 5/441 604/333 |
| 4,914,170 A * | 4/1990 | Chang .................. C08F 220/06 526/240 |
| 5,531,724 A * | 7/1996 | Young ..................... A61J 19/00 604/327 |
| 6,231,553 B1 * | 5/2001 | Hulett ..................... A61F 5/441 604/332 |
| 7,422,577 B2 * | 9/2008 | Udayakumar ...... A61L 28/0034 604/335 |
| 7,815,618 B2 * | 10/2010 | Schena ................. A61F 5/4407 604/350 |
| 8,167,857 B2 * | 5/2012 | James ..................... A61M 1/60 604/319 |
| 8,273,065 B2 * | 9/2012 | Gill ........................ A61F 5/4405 604/335 |
| 8,292,859 B2 * | 10/2012 | Salvadori .............. A61F 5/4405 604/327 |
| 8,357,105 B2 * | 1/2013 | Fontaine ................ A61B 5/208 600/580 |
| 8,912,298 B2 * | 12/2014 | Matsumoto ............. C07C 51/50 526/240 |
| 9,259,512 B2 * | 2/2016 | Udayakumar ...... A61L 28/0034 |
| 9,982,110 B2 * | 5/2018 | Hosomi .................. C07C 41/03 |
| 11,224,857 B2 * | 1/2022 | Tamaki ................ B01J 20/3085 |
| 11,459,431 B2 * | 10/2022 | Wada ...................... A61L 15/42 |

(Continued)

FOREIGN PATENT DOCUMENTS

| CN | 1696181 A | 11/2005 |
| CN | 106749803 A | 5/2017 |
| CN | 107501580 A * | 12/2017 ............. A61L 15/24 |

OTHER PUBLICATIONS

International Patent Application No. PCT/CN2018/092326; Int'l Search Report; dated Sep. 14, 2018; 2 pages.

*Primary Examiner* — Guy K Townsend
(74) *Attorney, Agent, or Firm* — BakerHostetler

(57) ABSTRACT

The present invention relates to a sodium polyacrylate super absorbent resin for blood absorption with a gradual hierarchical structure. When a blood simulant solution is used as the detection medium, according to ISO 19699-1:2017(E), the absorption capacity of the blood simulant solution is ≥18.0 g/g, Preferably ≥18.5 g/g; the absorption rate of the blood simulant solution is ≤45 s, preferably ≤40 s, more preferably ≤38 s; when human blood is used as the detection medium, according to ISO 19699-1:2017(E), the absorption capacity of the human blood is ≥8.0 g/g, preferably ≥8.3 g/g, more preferably ≥8.6 g/g; the absorption rate of the human blood is ≤45 s, preferably ≤40 s, more preferably ≤35 s, most preferably ≤25 s. The present invention combines organic cross-linking and inorganic cross-linking for surface modification, so that the resin has a gradual hierarchical structure, thereby ensuring that it has excellent blood absorption properties, while also having excellent water absorption properties and gel strength, and other performance.

6 Claims, No Drawings

(56) References Cited

U.S. PATENT DOCUMENTS

| | | | |
|---|---|---|---|
| 11,649,485 B2* | 5/2023 | Yin | C12Q 1/6841 719/328 |
| 11,753,675 B2* | 9/2023 | Ramachandran Iyer | C12Q 1/6886 719/328 |
| 11,926,867 B2* | 3/2024 | Yin | C12Q 1/6837 |
| 2004/0267216 A1* | 12/2004 | Udayakumar | A61F 5/441 604/333 |
| 2006/0183828 A1* | 8/2006 | Dairoku | B01J 20/3028 524/419 |
| 2006/0189962 A1* | 8/2006 | Burtoft | A61F 5/4405 604/334 |
| 2007/0238806 A1* | 10/2007 | Mitsukami | A61L 15/60 522/150 |
| 2008/0075937 A1* | 3/2008 | Wada | A61L 15/46 428/212 |
| 2009/0318885 A1* | 12/2009 | Dairoku | A61L 15/24 502/402 |
| 2010/0072421 A1* | 3/2010 | Kitano | A61L 15/24 525/330.3 |
| 2010/0120940 A1* | 5/2010 | Adachi | C08F 2/10 523/111 |
| 2012/0258851 A1* | 10/2012 | Nakatsuru | C08J 3/12 502/7 |
| 2013/0026412 A1* | 1/2013 | Machida | C08F 220/06 525/384 |
| 2014/0193641 A1* | 7/2014 | Torii | A61L 15/26 252/194 |
| 2015/0210843 A1* | 7/2015 | Kimura | B01J 20/267 525/187 |
| 2015/0217270 A1* | 8/2015 | Ueda | B01J 20/28011 502/402 |
| 2015/0225514 A1* | 8/2015 | Kimura | A61L 15/24 525/344 |
| 2017/0281425 A1* | 10/2017 | Herfert | A61F 13/535 |
| 2018/0071714 A1* | 3/2018 | Torii | B01J 20/261 |
| 2018/0304233 A1* | 10/2018 | Simonyan | C08J 3/245 |
| 2018/0305519 A1* | 10/2018 | Kamphus | C08K 7/00 |
| 2019/0070586 A1* | 3/2019 | Jiang | B01J 20/267 |
| 2020/0121521 A1* | 4/2020 | Daniel | A61F 13/53 |
| 2021/0268139 A1* | 9/2021 | Yang | C08J 3/245 |
| 2021/0285036 A1* | 9/2021 | Yin | C12Q 1/6841 |
| 2021/0369484 A1* | 12/2021 | Holden | A61F 5/445 |
| 2022/0033888 A1* | 2/2022 | Schnall-Levin | C12N 15/1065 |
| 2022/0296407 A1* | 9/2022 | Sims | A61F 5/441 |
| 2023/0129552 A1* | 4/2023 | Ramachandran Iyer | C12Q 1/6841 719/328 |
| 2023/0323434 A1* | 10/2023 | Yin | C12Q 1/6837 719/328 |

* cited by examiner

SUPER ABSORBENT RESIN AND PREPARATION METHOD THEREOF

CROSS-REFERENCE TO RELATED APPLICATION

This application is the National Stage of International Patent Application No. PCT/CN2018/092326, entitled HIGH-ABSORBABILITY RESIN AND PREPARATION METHOD THEREFOR, filed Jun. 22, 2018, the disclosures of which are incorporated herein by reference in their entireties.

TECHNICAL FIELD

The present invention relates to a super absorbent resin and preparation method thereof. Specifically, the present invention relates to a super absorbent resin for blood absorption with a gradual hierarchical structure, and more particularly, the present invention relates to a sodium polyacrylate super absorbent resin and preparation method thereof.

BACKGROUND OF THE INVENTION

Super absorbent resins, especially sodium polyacrylate super absorbent resins, have been widely used in sanitary products, such as sanitary napkins and diapers, due to their excellent water absorption and liquid absorption. In addition, they are also widely used in agriculture, industry, construction, medicine, and light Industry, chemical industry and other fields.

For super absorbent resins, they are generally required to have a higher absorption rate, excellent absorption speed, liquid permeability and higher gel strength when in contact with body fluids. After the previous particulate water absorption resin contacts with the aqueous solution, the surface is easy to bond and the particulate polymer is bonded into blocks, which is prone to "fish eyes", which causes the so-called gel blocking effect to hinder the further penetration of water molecules, it is not conducive to the full play of the water absorption performance of the resin, and affects its water absorption multiple and water absorption rate, etc. Another disadvantage of the particulate water absorption resin is that its gel strength is not high and cannot meet the needs of use. Later, in order to solve the problems mentioned above, people used variety of methods to improve the performance of water absorption resins, and surface cross-linking technology was one of them. This method improves the water absorption rate by chemically treating the surface of the water absorption resin, and overcomes the shortcomings of low gel strength, making it more valuable.

For example, U.S. Pat. No. 4,051,086 discloses that alcohols are used as dispersants and glyoxal is used as crosslinking agent for surface treatment, which can significantly improve the water absorption rate and gel strength of the resin, but the environmental protection problems of aldehydes are more prominent, especially difficult to apply to human hygiene products. European patent EP91302895.7 discloses that water absorption resin is placed in a high-speed stirrer, sprayed the treatment liquid prepared from a polyol crosslinking agent on the surface of the water absorption resin, and put it into an oven to heat the crosslinking reaction after stirring, this method greatly improves the water absorption rate, but requires expensive equipment Japanese patent JP7242709 discloses that the post-treatment liquid is dissolved in a hydrophilic solvent, heated to become a hot air flow, and the hot air flow passed through the heated resin powder to react on its surface, this method significantly improved the water absorption rate, but the treatment process was more complicated and difficult to operate. Moreover, the techniques disclosed in the above patent documents are all methods of surface cross-linking using a treatment liquid including a single cross-linking component, and the formed cross-linking layer is relatively simple, which makes it difficult to effectively solve the problems mentioned above.

In addition, Chinese patent CN 1696181A discloses the use of polyhydric alcohols or epoxy compounds for chemical crosslinking and the use of polyvalent metal salts for coordination crosslinking to treat sodium polyacrylate resin. Although it can achieve better results, there are compatibility problems between these two types of cross-linking methods. As a result, it is only a physical superposition of the two cross-linking methods without any necessary structural design, resulting in unsatisfactory overall performance and unable to guarantee that the performance indicators such as gel strength, water absorption multiple, and water absorption rate will be improved at the same time.

The most important thing is that these super absorbent resins as described above generally only have better water absorption properties. When these resins are used in applications such as sanitary napkins, surgical blood sucking and other occasions that need to absorb blood, the absorption rate and absorption capacity cannot meet the requirements of blood absorption performance. The reason is that the above-mentioned resins can only effectively absorb the water in the blood. When the water in the blood is absorbed, other substances will easily coagulate into blocks, which greatly hinders the experience of comfort and other aspects, and the absorption rate, absorption capacity, etc., cannot meet the requirements of blood absorption performance.

SUMMARY OF THE INVENTION

In order to solve the above-mentioned technical problems, the inventors developed a new super absorbent resin, which combines organic cross-linking and inorganic cross-linking for surface modification, so that the resin has a gradual hierarchical structure. While achieving excellent blood absorption performance, it has good gel strength and other properties.

In the first aspect, the present invention relates to a super absorbent resin, when blood simulant solution is used as the detection medium, according to ISO 19699-1:2017(E), the blood absorption capacity of the blood simulant solution is ≥18.0 g/g, preferably ≥18.5 g/g; the blood absorption rate is ≤45 s, preferably ≤40 s, more preferably ≤38 s.

When human blood is used as the detection medium, according to ISO 19699-1:2017(E), the human blood absorption capacity is ≥8.0 g/g, preferably ≥8.3 g/g, more preferably ≥8.6 g/g; the human blood absorption rate is ≤45 s, preferably ≤40 s, more preferably ≤35 s, most preferably ≤25 s.

Wherein, with respect to the above-mentioned first aspect, in a preferred embodiment, the residual monomer content of the super absorbent resin, calculated as acrylic acid, is ≤1000 mg/kg; the volatile content is ≤10.0%; the pH is 5.0-8.0; with regard to the particle size distribution, the content of the sample with particle size <150 μm is ≤5 wt %, the content of sample with particle size <106 μm is ≤1 wt %; the bulk density is 0.65 g/cm$^3$-0.80 g/cm$^3$; and/or whiteness is ≥70%.

In a preferred embodiment, the super absorbent resin is a surface-modified sodium polyacrylate resin.

In the second aspect, the present invention relates to a method for preparing the super absorbent resin, which includes the following steps:
(1) weigh the surface dispersant;
(2) weigh the polyvalent metal salt, preferably aluminum salt, calcium salt, magnesium salt or zinc salt, more preferably aluminum salt, prepare it into solution A;
(3) weigh the compound containing epoxy groups, prepare it into solution B;
(4) mix the surface dispersant, solution A and solution B, and sodium polyacrylate resin;
(5) carry out the cross-linking reaction to obtain a surface-modified sodium polyacrylate super absorbent resin with a gradual hierarchical structure.

Wherein, the sodium polyacrylate resin is an absorbent resin with an internal crosslinked structure which hasn't been surface modified, and the sodium polyacrylate super absorbent resin is a surface modified (surface crosslinked) super absorbent resin of the present invention. The particle size of the sodium polyacrylate resin used in the present invention is preferably 120 μm-830 μm, more preferably 150 μm-380 μm.

In a preferred embodiment, the surface dispersant is selected from methanol, ethanol, acetone or fumed silica, preferably methanol or ethanol. The mass ratio of the surface dispersant to the sodium polyacrylate resin is (1-15):100, preferably (1-10):100, and more preferably (1-5):100.

In a preferred embodiment, the aluminum salt of solution A is selected from aluminum chloride, aluminum sulfate, aluminum ammonium sulfate, aluminum nitrate and alum, preferably aluminum sulfate or aluminum ammonium sulfate. The solvent of solution A is selected from water, acetone and polyols; preferably water and/or glycerol, and the mass ratio of glycerol to water is (0-0.7):1. The mass concentration of the aluminum salt in solution A is 3%-25%, preferably 8%-25%, more preferably 10%-20%. The mass ratio of aluminum salt to sodium polyacrylate resin is (0.010-0.050):1, preferably (0.025-0.030):1

The role of the aluminum salt is to form coordination crosslinking on the surface of the resin. If the dosage is too low, the cross-linked layer will be too loose and the effect of crosslinking modification cannot be achieved; if the dosage is too high, the cross-linked layer will be too tight and the pore size will decrease, thereby reducing the absorption capacity and slowing the absorption rate.

In a preferred embodiment, the compound containing epoxy groups of solution B is selected from epoxy resin, epichlorohydrin, propylene oxide, glycidyl ether, polyethylene glycol diglycidyl ether and ethylene glycol diglycidyl ether; preferably epichlorohydrin, glycidyl ether or polyethylene glycol diglycidyl ether. The solvent of solution B is selected from alcohols and ketones; preferably methanol, ethanol, isopropanol, acetone or methyl ethyl ketone; more preferably ethanol or methanol. The mass concentration of the compound containing epoxy groups in solution B is 10%-25%. The mass ratio of the compound containing epoxy groups to the sodium polyacrylate resin is (0.001-0.006):1, preferably (0.002-0.004):1, more preferably 0.003:1.

The content of the compound containing epoxy groups in solution B determines the content of the resin dense cross-linked layer and the size of the pores. If the content is too low, the cross-linked layer will become loose and the gel strength cannot be guaranteed. If the content is too high, it will make the cross-linked layer too dense, although the gel strength increases, but it will seriously affect the absorption capacity and absorption rate.

The mass ratio of the aluminum salt of solution A, the compound containing epoxy groups of solution B and the sodium polyacrylate resin is as important as the mass concentration of aluminum salt in solution A and the mass concentration of compounds containing epoxy group in solution B. They are all to form a gradual hierarchical structure with suitable crosslinking density on the surface of the sodium polyacrylate resin to ensure that the resin has excellent comprehensive properties.

In a preferred embodiment, in step (4), the surface dispersant, solution A, solution B are mixed uniformly, and then mixed with sodium polyacrylate resin; or, the surface dispersant, solution A, solution B are mixed with sodium polyacrylate resin in sequence; or, the surface dispersant, solution B, solution A are mixed with sodium polyacrylate resin in sequence; or, the surface dispersant and the solution B are mixed uniformly with the sodium polyacrylate resin, and then the solution A and the previously obtained mixture are mixed uniformly. Preferably, the surface dispersant and solution B are mixed firstly, and then mix with the sodium polyacrylate resin uniformly at room temperature; subsequently, the solution A is heated to 60-100° C., preferably 60-80° C., and mixed uniformly with the mixture obtained as described above at the said temperature.

In a preferred embodiment, the temperature of the cross-linking reaction in step (5) is 50-200° C., preferably 80-185° C., more preferably 120-140° C.; the time is 20-210 min, preferably 25-120 min, more preferably 30-90 min. When manually putting materials into and out of the heating equipment, the operating time is not within the time range above mentioned; when heating in continuous automated production equipment, the time between the automatic input and output heating equipment of the materials is not within the time range above mentioned.

In the third aspect, the present invention relates to a super absorbent product comprising the super absorbent resin of the present invention.

In a preferred embodiment, the product may be, for example, sanitary napkins, medical blood-absorbing products, and the like.

In the fourth aspect, the present invention relates to the use of the product in blood absorption.

The present invention combines the organic cross-linking and inorganic cross-linking of the surface modification of the super absorbent resin, and this combination is not a simple physical superposition, but an innovative "organic" combination. Two modification solutions A and B are sprayed on the surface of super absorbent resin successively. Modification solution A is mainly inorganic coordination cross-linking, it is relatively loose and can form a relatively "soft" cross-linked layer, and modification solution B is an epoxy compound that is prone to chemical cross-linking, which can form a relatively "hard" cross-linked layer with a relatively large degree of cross-linking. After the treatment liquids of A and B are sprayed separately, they are heat treated together for a certain period of time to complete the two crosslinking reactions. Due to the ingenious design of this feeding process and post-treatment process, on the one hand, the two cross-linked layers have an inner and outer sequence, that is, the denser cross-linked layer is in the core layer, which ensures the gel strength of the resin, and the looser cross-linked layer is in the shell layer, which ensures the water absorption channel and the water absorption rate. On the other hand, due to the use of multi-step processing technology, the distribution of the two layers, as a result of diffusion, presents a gradual hierarchical structure, rather than a completely isolated two-layer structure, so as to achieve the perfect combination of water absorption rate and gel strength. At the same time, the formation of this gradual hierarchical structure also enables large molecules such as proteins in the blood to penetrate into the resin together with water and other small molecules through its microscopic pores, to ensure its excellent blood absorption performance, fast absorption, and high gel strength and viscous liquid absorption capacity.

Obviously, this method combines the advantages of the existing technology, and its process is simpler, easy to operate, and does not require special processing equipment, thereby greatly reducing the cost.

DETAILED DESCRIPTION OF THE INVENTION

Hereinafter, the embodiments of the present invention will be further described, wherein each embodiment is only an exemplary and/or preferred embodiment of the present invention, and is not intended to constitute a limitation on the scope of the present invention. Those skilled in the art can make many different improvements and modifications based on the above description and the following description of the embodiments, which will not depart from the spirit and essence of the present invention.

Accordingly, the scope of the present invention is only intended to be limited by the scope of protection required by the claims.

Example 1

(1) Weigh methanol, the mass ratio of methanol to sodium polyacrylate resin is 1:20;
(2) Weigh aluminum sulfate and prepare it into aqueous solution A with a mass concentration of 25%; the mass ratio of aluminum sulfate to sodium polyacrylate resin is 0.025:1;
(3) Weigh polyethylene glycol diglycidyl ether and prepare it into ethanol solution B with a mass concentration of 20%; the mass ratio of polyethylene glycol diglycidyl ether to sodium polyacrylate resin is 0.0030:1;
(4) Methanol and solution B are well mixed firstly, then mixed uniformly with sodium polyacrylate resin at room temperature; then, solution A is heated to 60° C. and mixed with the mixture above mentioned uniformly at 60° C.;
(5) The resin processed in step (4) is put into a tray, entered an oven for cross-linking reaction, the reaction temperature is 120° C., and the reaction time is 90 minutes, to obtain the surface-modified super absorbent resin of the present invention.

Example 2

The concentration of solution A in Example 1 is changed to 20%, the concentration of solution B is 25%. The others are the same as in Example 1.

Example 3

The solution A in Example 1 is changed to an aqueous solution of ammonium alum (ammonium aluminum sulfate dodecahydrate) with a mass concentration of 25%. Entered into the oven for cross-linking reaction, the reaction temperature is 140° C., the reaction time is 60 minutes. The others are the same as in Example 1.

Example 4

The solution A in Example 2 is changed to an aqueous solution of ammonium alum (ammonium aluminum sulfate dodecahydrate) with a mass concentration of 20%. Entered into the oven for cross-linking reaction, the reaction temperature is 140° C., the reaction time is 60 minutes. The others are the same as in Example 2.

Example 5

The solution A in Example 4 is changed to a solution of ammonium alum (ammonium aluminum sulfate dodecahydrate) in water and glycerol, the mass concentration of which is 11%, and the mass ratio of glycerol to water is 1:6. Enter the oven for cross-linking reaction, the reaction temperature is 140° C., and the reaction time is 50 minutes. The others are the same as in Example 4.

Example 6

The mass ratio of methanol to sodium polyacrylate resin in Example 1 is changed to 1:50, solution B is changed to an ethanol solution with an epichlorohydrin mass concentration of 25%, and the solvent of solution A was glycerol and water, the mass ratio of glycerol to water is 3:5. The others are the same as in Example 1.

Example 7

The solution A in Example 6 is changed to a solution of ammonium alum (ammonium aluminum sulfate dodecahydrate) in water and glycerol, with a mass concentration of 11%, and the mass ratio of glycerol to water was 1:6. Entered the oven for cross-linking reaction, the reaction temperature is 140° C., and the reaction time is 50 minutes. The others are the same as in Example 6.

Example 8

The surfactant in Example 7 is changed to ethanol, and the mass ratio of ethanol to sodium polyacrylate resin is changed to 3:100. The others are the same as in Example 7.

Example 9

After mixing methanol, solution A, and solution B in Example 1, they were mixed with sodium polyacrylate resin and mixed uniformly. Solution A is changed to alum aqueous solution, and the mass ratio of methanol to sodium polyacrylate resin is changed to 1:10. Other conditions are the same Example 1.

Example 10

The methanol, solution B, and solution A in Example 1 were mixed with sodium polyacrylate resin in sequence, and the solution A is changed to an aqueous solution of aluminum nitrate. Other conditions are the same as in Example 1.

Example 11

After mixing the methanol, solution A, and solution B in Example 3, they are mixed with sodium polyacrylate resin and mixed uniformly. The compound containing epoxy group of solution B is changed to glycidyl ether, the mass ratio of glycidyl ether to sodium polyacrylate resin is 0.0060:1. Other conditions are the same as in Example 3.

Example 12

The methanol, solution B, and solution A in Example 3 are mixed with the sodium polyacrylate resin in sequence. Other conditions are the same as in Example 3.

Example 13

The mass ratio of methanol to sodium polyacrylate resin in Example 1 is changed to 3:20, the reaction temperature is changed to 185° C., the reaction time is 20 minutes, and the solution B is changed to a methanol solution of epichlorohydrin with a mass solubility of 10%, the ratio of propylene oxide to sodium polyacrylate resin is 0.00101. Other conditions are the same as in Example 1.

Example 14

The mass concentration of aluminum sulfate in solution A in Example 1 is changed to 10%, and the mass ratio of aluminum sulfate to sodium polyacrylate resin is changed to 0.010'1. Other conditions are the same as in Example 1.

Example 15

The mass concentration of ammonium alum of solution A in Example 3 is changed to 3%, and the mass ratio of ammonium alum to polyacrylic acid resin is changed to 0.045:1. Other conditions were the same as in Example 3.

Example 16

The heating temperature of solution A in Example 1 is changed to 80° C., the heating temperature in step (5) is changed to 80° C., and the time is changed to 180 minutes. Other conditions are the same as in Example 1.

Comparative Example 1

The specific process is carried out as disclosed in CN 1696181A, and the steps are as follows:
1)、Preparation of Treatment Solution A:
  Choose acetone as the dispersant, epichlorohydrin as the cross-linking agent, and DMP-30 as the cross-linking accelerator; put the dispersant, cross-linking agent, and cross-linking accelerator in a glass container and stir to prepare treatment solution A. The mass concentration of epichlorohydrin is 12%;
2)、Preparation of Treatment Solution B:
  Put the deionized water in a glass container and heat it to 90° C., weigh the aluminum sulfate salt and the second cross-linking agent glycerin, add the deionized water and stir to prepare treatment solution B, the mass concentration of aluminum sulfate is 15%;
3)、Treatment of Resin by Treatment Liquid:
  Weigh 60 kg of sodium polyacrylate resin and place it in a 300 rpm stirrer. While stirring, spray treatment liquid A and treatment liquid B on the surface of the water absorption resin in sequence, and then put the resin into the tray and heat it in the oven for crosslinking reaction, the reaction temperature is 120° C., the reaction time is 100 minutes, and the surface modification of the sodium polyacrylate resin is obtained.

Hereinafter, various properties/indices and test methods of the super absorbent resin of the present invention prepared according to Examples 1-16 and the sodium polyacrylate resin prepared according to Comparative Example 1 will be described in detail.

1、Blood Absorption Capacity, Blood Absorption Rate and Gel Strength

The detection medium uses human blood and blood simulant solution respectively to test the blood absorption capacity and the blood absorption rate of the super absorbent resin of the present invention.

Human blood was purchased from hospital, and its blood absorption capacity and blood absorption rate were tested according to the test method described in ISO 19699-1:2017 (E) (replace the blood simulant solution in the test method described in ISO 19699-1:2017(E) with human blood for testing), the specific method is as follows.

The blood simulant solution is prepared according to the preparation method described in ISO 19699-1:2017(E), and the test method is according to the test method of the blood absorption capacity and blood absorption rate described in ISO 19699-1:2017(E). The specific method is as follows.

Physical Properties of Human Blood:

After testing, the corresponding parameters of human blood used in the present invention are as follows:

| Property | Value | Standard |
|---|---|---|
| Density | (1.04-1.05) g/ml | GB/T 22230-2008 ISO 758 |
| Viscosity | (3.2-4.4) mPa · s | GB/T 5561-2012 ISO 6388 |
| pH value | 6.35-7.35 | GB/T9742-2007 ISO 6353-1 |

Preparation Method of Blood Simulant Solution:
A.1 Principle

The blood simulant solution is formulated according to the main physical properties of human blood, which has similar flow and viscosity characteristics, and can well simulate the performance of human blood.

A.2 Formula

Unless otherwise specified, the following reagents can only be used with reagents marked as chemically pure. The chemical composition of the blood simulant solution includes the following substances:

| | |
|---|---|
| Deionized water (three grade water specified in ISO3696): | 860.000 g ± 1.000 g |
| Sodium chloride: | 10.000 g ± 0.010 g |
| Sodium carbonate: | 40.000 g ± 0.040 g |
| Glycerol (glycerin): | 140.0 ml |
| Sodium benzoate: | 1.000 g ± 0.001g |
| Blue pigment: | 0.050 ml |
| Sodium carboxymethyl cellulose (molecular weight 25000): | 5.000 g ± 0.005 g |
| Standard modifier (non-ionic polymeric fluorine-containing surfactant): | 10.0 ml |

A.3 Physical Properties of Blood Simulant Solution

At (23±1)° C., the blood simulant solution will meet the requirements in the following table:

| Property | Value | Standard |
|---|---|---|
| Density | (1.05 ± 0.05) g/ml | GB/T 22230-2008 ISO 758 |
| Viscosity | (7.3 ± 1.1) mPa · s | GB/T 5561-2012 ISO 6388 |
| Surface Tension | (40 ± 4) mN/m | GB/T 22237-2008 EN 14370 |
| pH value | 11.0 ± 0.1 | GB/T9742-2007 ISO 6353-1 |

A.4 Preparation Method
- A.4.1 Weigh 10.00 g sodium chloride, 40.00 g sodium carbonate, 1.00 g sodium benzoate, 5.00 g sodium carboxymethylcellulose with an analytical balance, and pour them into a 2000 mL beaker in turn;
- A.4.2 Use a 250 ml graduated cylinder to measure 140.00 ml glycerol and pour it into the beaker in A.4.1, and use an analytical balance to weigh 860 g deionized water into the beaker, and stir evenly.
- A.4.3 Use a 500 ml graduated cylinder to measure 300 ml of the mixture in A.4.2 each time, pour it into the mixer, turn on the switch and start timing with a stopwatch, stir for 7 minutes, turn off the switch, pour out the mixture, and stir the remaining mixture in this way.
- A.4.4 The mixed liquid after stirring in A.4.3 is stirred once again with a stirrer according to the method in A.4.3, and then 10.0 ml standard vehicle and 0.05 ml blue pigment are added to the stirred liquid, and the mixture is evenly stirred and left for 24 hours before use.

Method for Measuring the Absorption of Blood Simulant Solution:

B.1 General Principles

In the blood simulant solution, the amount of liquid absorbed by the super absorbent resin for absorbing blood in a certain period of time is measured by the weighing method.

B.2 Reagent

B.2.1 Blood simulant solution

The blood simulant solution should be prepared as described above.

B.3 Equipment
- B.3.1 Analytical balance: the range is 100 g, and the sensitivity is 0.0001 g.
- B.3.2 Nylon tea bag: The size is 100 mm×150 mm, the bag is made of nylon filter cloth with a pore size of 300 mesh, and the basis weight is 58 g/m².
- B.3.3 Glass beaker: 2000 ml capacity.
- B.3.4 Timer: The timing range is 60 min, accurate to 0.1 s.
- B.3.5 Drying rack with clamping wire and clamp.
- B.3.6 Thermometer: The range is 100° C.

B.4 Sampling

To ensure that the samples taken from large bags or containers are representative, the top layer (approximately 20 cm) should be removed. A spoon is used to take 500 grams of the test sample, and it is placed in a suitable airtight container within 3 minutes after taking it.

Before the sample is tested, the sample should be placed in a closed container to reach equilibrium with the laboratory environment temperature. The recommended test conditions refer to ISO291. If the above conditions are not met, the temperature and relative humidity should be recorded.

B.5 Measurement Procedure
- B.5.1 Weigh (1.000±0.005) g sample, accurate to 0.0001 g, and record the mass of the sample as $m_0$, pour all the sample into the tea (4.8.3.2) and spread it flat on the bottom of the tea bag (the sample attached to the inside of the tea bag should also be poured into the bottom of the tea bag), and heat stitched about 3-5 cm along the edge of the opening of the tea bag.
- B.5.2 Fill a glass beaker (4.8.3.3) with 1800 mL of blood simulant solution (4.8.2.1), put the tea bags into the beaker containing the blood simulant solution according to the number, so that the liquid is immersed in the tea bag and the height is 2.0 cm, and press count down with a stopwatch. (Each beaker puts at most 2 groups, that is, 4 tea bags).
- B.5.3 After 30 minutes, take out the tea bags in sequence according to their numbers, fold the upper left corner of the tea bags down for about ½, and hang them on the drying rack with a clip, and hang them at an angle of about 45°.
- B.5.4 After hanging for 10 minutes, take down the weighing mass in the order of hanging and mark it as $m_1$. When multiple samples are tested at the same time, they cannot touch each other.
- B.5.5 According to the above method, the blank value of the teabag used above is measured without placing the sample, and the mass of the blank teabag after absorbing the liquid is recorded as $m_2$.

B.6 Display of Measurement Results

The absorption capacity of the blood simulant solution can be calculated according to formula (4):

$$m = \frac{m_1 - m_2 - m_0}{m_0} \quad (4)$$

wherein:

m—The amount of blood simulant solution absorbed by the sample, in grams per gram (g/g);

$m_1$—The mass of the tea bag containing the sample after absorbing the liquid, in grams (g);

$m_2$—The mass of the blank test teabag, in grams (g);

$m_0$—The mass of the sample to be weighed, in grams (g);

Perform two measurements at the same time, and take the arithmetic mean value as the measurement result, and the result should be rounded to one decimal place.

Method for measuring absorption rate of blood simulant solution:

C.1 General Principles

In the blood simulant solution, the rate of absorption of the blood simulant solution was measured by the liquid no-flow method, and the time required for 1 g of sodium polyacrylate resin to absorb 5.0 ml of the blood simulant fluid.

C.2 Reagent
- C.2.1 Blood simulant solution should be prepared as described above.

C.3 Equipment
- C.3.1 Analytical balance: the range is 100 g and the accuracy is 0.0001 g.
- C.3.2 Glass beaker: 100 mL capacity.
- C.3.3 Glass measuring cylinder, type A or B (laboratory glass products) with a capacity of 5.0 mL (accurate to 0.1 ml).
- C.3.4 Timer. The timing range is 60 min, accurate to 0.1 s.

C.4 Sampling

Appropriate protective equipment should be used when handling samples over 10 g, such as a dust mask or a fume hood.

To ensure that the samples taken from large bags or containers are representative, the top layer (approximately 20 cm) should be removed. Use a spoon to take 1,000 grams of the test sample, and place it in a suitable airtight container within 3 minutes after taking it.

Before the sample is tested, the sample should be placed in a closed container to reach equilibrium with the laboratory environment temperature. The recommended test condition temperature is (23±1)° C. and relative humidity is (50±10)% (ISO 291, class II).

C.5 Test Steps

Perform at least two tests according to the following procedure:

C.5.1 Use an analytical balance (C.3.1) to weigh (1.000±0.005) g of the sample to be tested, accurate to 0.001 g, and pour it into a beaker (C.3.2).

C.5.2 Shake or tap the beaker by hand to spread the sample evenly on the bottom of the beaker.

C.5.3 Use a graduated cylinder (C.3.3) to measure 5.0 mL of blood simulant solution (C.2.1) at (23±1)° C. Pour into the center of the bottom (C.5.2) (control the speed so that the liquid does not splash on the inner wall of the beaker when pouring) and start timing at the same time.

C.5.4 When the fluidity of the liquid in the cup disappears, stop the stopwatch and record the elapsed time t.

One way to determine complete absorption is to tilt the beaker slightly and observe whether there is liquid flow.

C.6 Presentation of the Results

Calculate the arithmetic average based on the measured value of the simulated blood absorption rate, and round it to an integer, expressed in seconds.

The absorption rate of blood simulant solution is calculated by the time it takes to absorb 5.0 ml of blood simulant solution with 1 g SAP.

The gel strength was tested according to the method described in the literature reported by Zhu Youliang et al. (Zhu Youliang, Wu Guoqiang, Synthesis of water absorption resin with core-shell structure, Plastics, 2005, 34(1):23-26 (朱友良, 吾国强, 具有核壳型结构吸水树脂的合成, 塑料, 2005, 34(1):23-26)). The test results are shown in Table 1.

TABLE 1

Resin performance test results

| | Absorption capacity of blood simulant solution (g/g) | Absorption rate of blood simulant solution (s) | Gel strength | Absorption capacity of human blood (g/g) | Absorption rate of human blood (s) | Gel strength |
|---|---|---|---|---|---|---|
| Example 1 | 18.6 | 37 | excellent | 8.0 | 27 | excellent |
| Example 2 | 19.0 | 36 | excellent | 8.5 | 23 | excellent |
| Example 3 | 18.8 | 37 | excellent | 8.3 | 25 | excellent |
| Example 4 | 18.5 | 38 | excellent | 8.6 | 30 | excellent |
| Example 5 | 18.7 | 37 | excellent | 8.5 | 32 | excellent |
| Example 6 | 18.7 | 37 | excellent | 8.7 | 33 | excellent |
| Example 7 | 18.3 | 39 | excellent | 8.3 | 32 | excellent |
| Example 8 | 18.6 | 39 | excellent | 8.6 | 36 | excellent |
| Example 9 | 18.3 | 44 | excellent | 8.3 | 40 | excellent |
| Example 10 | 18.1 | 45 | excellent | 8.7 | 45 | excellent |
| Example 11 | 18.1 | 45 | excellent | 8.6 | 45 | excellent |
| Example 12 | 18.2 | 44 | excellent | 8.2 | 43 | excellent |
| Example 13 | 18.4 | 42 | excellent | 8.4 | 42 | excellent |
| Example 14 | 18.0 | 41 | excellent | 8.0 | 41 | excellent |
| Example 15 | 18.4 | 43 | excellent | 8.4 | 43 | excellent |
| Example 16 | 18.2 | 42 | excellent | 8.2 | 42 | excellent |
| Comparative example 1 | 4.3 | 110 | excellent | 2.3 | 220 | excellent |

It can be clearly seen from the data listed in Table 1 that the super absorbent resin of the present invention has excellent absorption performance and gel strength regardless of whether the detection medium is a blood simulation solution or real human blood for testing. Among them, the amount of blood absorption is significantly higher than that of the comparative example, and the blood absorption rate is much faster than that of the comparative example.

2、Residual Monomer

According to GB/T20405.2-2006, the monomer residual amount of the super absorbent resin in examples 1-8 of the present invention (calculated as acrylic acid) is ≤800 mg/kg; the residual monomer of the super absorbent resin in examples 9-16 of the present invention (calculated as acrylic acid) is ≤1000 mg/kg.

3、Volatile Content

According to GB/T20405.4-2006, the volatile of the super absorbent resin in Examples 1-16 of the present invention is ≤10.0%.

4、pH Value

According to GB/T20405.1-2006, the pH value of the super absorbent resins of Examples 1-16 of the present invention is ≥5.0 and ≤8.0.

5、Particle Size Distribution

The test method is as follows:

5.1 General Principles

Through a series of standard sieves, the quantitative super absorbent resin is divided into several specific particle size components. Weigh each component and report it as a percentage of the total.

5.2 Equipment 5.2.1 Analytical balance: 1000 g range, 0.01 g accuracy.

5.2.2 Beaker: made of glass or plastic, with a capacity of 250 mL 5.2.3 Vibrating screen machine: Retsch VE1000 and equivalent types. It can be loaded with 3 standard sieves with a diameter of 200 mm, with bottom collecting pan and upper cover, grounded to prevent static electricity.

5.2.4 Standard sieve: a stainless steel sieve with a diameter of φ200 mm, with apertures of 45 μm, 106 μm, 150 μm, with a bottom collecting pan and upper cover.

5.2.5 Brush: made of camel hair. Used to clean standard sieve.

5.2.6 Stopwatch: measuring range 60 min, accurate to 0.1 s.

5.3 Sampling

Warning: Use appropriate protective equipment, such as dust mask or fume hood, when handling samples over 10 g.

In order to ensure that the samples taken from large bags or containers are representative, the uppermost layer (approximately 20 cm) should be removed. Use a spoon to sample and place it in a suitable closed container within 3 minutes after sampling.

Before the sample is tested, the sample should be placed in a closed container to reach equilibrium with the laboratory environment temperature. The recommended test conditions are: (23±2)° C., relative humidity (50±10)%. If the above conditions are not met, the temperature and relative temperature should be recorded.

Before taking the sample out of the container for testing, shake the container 3 to 5 times to ensure that the sample is even, then leave it for 5 minutes, open the lid and take out the sample.

5.4 Steps 5.4.1 Make sure the sieve is dry. Lightly inspect each sieve for damage and cleanliness. The sieve should be replaced if damaged. Use a brush to remove residual particles on the sieve.

5.4.2 Place the bottom plate and the sieve on a standard vibrating machine in the order of bottom plate, 45 μm, 106 μm, and 150 μm from bottom to top.

5.4.3 Weigh (100±0.01) g of the super absorbent resin sample, record it as m, and put it into a beaker.

5.4.4 Pour all the samples in the 5.4.3 beaker into the top sieve.

5.4.5 Cover the upper cover and seal it according to the standard vibrating screen machine instructions.

5.4.6 Ensure that the equipment is grounded to prevent static electricity.

5.4.7 Set up the vibrating screen machine according to the following conditions:
Strength: (70±2)% (set for Retsch VE1000).
Amplitude: 1.0 mm
Oscillation time: 10 min.

5.4.8 Start the vibrating screen machine. After shaking for 10 minutes, weigh the mass of the sample remaining on the 106 μm sieve as $m_1$, the mass of the sample remaining on the 45 μm sieve as $m_2$, and the mass of the sample remaining on the bottom plate as $m_3$.

5.5 Calculation

The percentage of each part is calculated according to the following formula:

Sample content below the 150 μm screen: $X_1 = [(m_1 + m_2 + m_3)/m_s]*100\%$

Sample content below the 106 μm screen: $X_2 = [(m_2 + m_3)/m_s]*100\%$

Sample content below the 45 μm screen: $X_3 = [m_3/m_s]*100\%$ wherein:

$X_1$—The content of the sample below the 150 μm screen, expressed in %;

$m_1$—The mass of the sample remaining on the 106 μm sieve, expressed in g;

$m_2$—The mass of the sample remaining on the 45 μm sieve, expressed in g;

$m_3$—The mass of the sample remaining on the chassis, expressed in g;

$m_s$—The total mass of the sample, expressed in g;

$X_2$—The content of the sample below the 106 μm screen, expressed in %;

$X_3$—The content of the sample below the 45 μm screen, expressed in %;

Perform two measurements at the same time, and take the arithmetic mean value as the measurement result, and round the result to one decimal place.

After measurement, the particle size distribution of the super absorbent resins of Examples 1-16 of the present invention is ≤5% (the content of samples with a particle diameter of <150 μm), and ≤1% (the content of samples with a particle diameter of <106 μm).

6、Bulk Density

According to ISO17190-9, the bulk density of the super absorbent resin in Examples 1-16 of the present invention is ≥0.65 g/cm³ and ≤0.80 g/cm³.

7、Whiteness

According to GB/T22427.6-2008, the whiteness of the super absorbent resins of Examples 1-16 of the present invention is ≥70%.

Obviously, the above-mentioned embodiments are merely examples for clear description, and are not intended to limit the implementation. For those of ordinary skill in the art, other modifications or changes in different forms can be made on the basis of the above description. There is no need and cannot give an exhaustive list of all implementation methods. The obvious changes or modifications derived from this are still within the protection scope of the present invention.

What is claimed is:

1. A super absorbent resin having an absorption capacity of a blood simulant solution when the blood stimulant solution is used as a detection medium of greater than or equal to 18.0 g/g, according to ISO 19699-1:2017 (E), with an absorption rate of the blood simulant solution of less than or equal to 45 seconds.

2. A super absorbent resin having an absorption capacity of human blood when the human blood is used as a detection medium of greater than or equal to 8.0 g/g, according to ISO 19699-1:2017 (E), with an absorption rate of the human blood of less than or equal to 45 seconds.

3. The super absorbent resin according to claim 2 having an absorption capacity of a blood simulant solution when the blood stimulant solution is used as a detection medium of greater than or equal to 18.0 g/g, according to ISO 19699-1:2017 (E), with an absorption rate of the blood simulant solution of less than or equal to 45 seconds.

4. The super absorbent resin according to claim 1, wherein the super absorbent resins has a residual monomer content of ≤1000 mg/kg, calculated as acrylic acid; a volatile content of ≤10.0%; a pH value of 5.0-8.0; a particle size distribution wherein a proportion of particles with a size of <150 μm is ≤5 wt %, and a proportion of particles with a size of <106 μm is ≤1 wt %; a bulk density of 0.65 g/cm³-0.80 g/cm³; a whiteness of ≥70%, or any combination thereof.

5. The super absorbent resin according to claim 1, wherein the super absorbent resin comprises surface modified sodium polyacrylate resin.

6. The super absorbent resin according to claim 5, wherein the super absorbent resin is surface modified by surface crosslinking using a solution A comprising a polyvalent metal salt, and using a solution B that is prepared from compounds containing epoxy groups and solvents.

* * * * *